US00PP18938P2

(12) United States Plant Patent
Smith

(10) Patent No.: US PP18,938 P2
(45) Date of Patent: Jun. 17, 2008

(54) ***HIBISCUS* PLANT NAMED 'BRANDY PUNCH'**

(50) Latin Name: ***Hibiscus* hybrid**
Varietal Denomination: Brandy Punch

(75) Inventor: Mark A. Smith, Fort Myers, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/641,530

(22) Filed: Dec. 18, 2006

(51) Int. Cl.
*A01H 5/00* (2006.01)

(52) U.S. Cl. ..... Plt./257

(58) Field of Classification Search ..... Plt./257
See application file for complete search history.

(56) References Cited

PUBLICATIONS

UPOV ROM GTITM Computer Database, GTI Jouve Retrieval Software 2007/02 Citation for 'Brandy Punch'.*

* cited by examiner

*Primary Examiner*—Wendy C. Haas
(74) *Attorney, Agent, or Firm*—C. A. Whealy

(57) ABSTRACT

A new and distinct cultivar of Hardy *Hibiscus* plant named 'Brandy Punch', characterized by its upright and outwardly spreading plant habit; green and purple-colored leaves that are palmately lobed; early flowering habit; and large single dark pink-colored flowers.

1 Drawing Sheet

Botanical designation: *Hibiscus* hybrid.
Cultivar denomination: 'Brandy Punch'.

BACKGROUND OF THE INVENTION

The present invention relates to a new and distinct cultivar of *Hibiscus,* botanically known as *Hibiscus* hybrid, commercially referred to as Hardy *Hibiscus* and hereinafter referred to by the name 'Brandy Punch'.

The new *Hibiscus* is a product of a planned breeding program conducted by the Inventor in Alva, Fla. The objective of the breeding program is to create new freely-branching Hardy *Hibiscus* cultivars with a compact plant habit and desirable flower color.

The new Hardy *Hibiscus* originated from a cross-pollination made by the Inventor in Alva, Fla. during the spring of 2002, of the *Hibiscus* hybrid cultivar Carafe Yogrenache, disclosed in U.S. Plant Pat. No. 17,571, as the female, or seed, parent with the *Hibiscus* hybrid cultivar Kopper King, disclosed in U.S. Plant Pat. No. 10,793, as the male, or pollen, parent. The cultivar Brandy Punch was discovered and selected by the Inventor as a flowering plant within the progeny of the stated cross-pollination in a controlled environment in Alva, Fla. during the spring of 2003.

Asexual reproduction of the new Hardy *Hibiscus* by vegetative terminal cuttings in a controlled environment in Alva, Fla. since June, 2003, has shown that the unique features of this new Hardy *Hibiscus* are stable and reproduced true to type in successive generations.

SUMMARY OF THE INVENTION

The cultivar Brandy Punch has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Brandy Punch'. These characteristics in combination distinguish 'Brandy Punch' as a new and distinct cultivar of Hardy *Hibiscus:*

1. Upright and outwardly spreading plant habit.
2. Green and purple-colored leaves that are palmately lobed.
3. Early flowering habit.
4. Large single dark pink-colored flowers.

Plants of the new Hardy *Hibiscus* can be compared to plants of the female parent, the cultivar Carafe Yogrenache. In side-by-side comparisons conducted in Alva, Fla., plants of the new Hardy *Hibiscus* differed from plants of the cultivar Carafe Yogrenache in the following characteristics:

1. Plants of the new Hardy *Hibiscus* were taller than plants of the cultivar Carafe Yogrenache.
2. Plants of the new Hardy *Hibiscus* and the cultivar Carafe Yogrenache differed in leaf form and color.
3. Flowers of plants of the new Hardy *Hibiscus* were more faded pink in color than flowers of plants of the cultivar Carafe Yogrenache.

Plants of the new Hardy *Hibiscus* can be compared to plants of the male parent, the cultivar Kopper King. In side-by-side comparisons conducted in Alva, Fla., plants of the new Hardy *Hibiscus* differed from plants of the cultivar Kopper King in the following characteristics:

1. Plants of the new Hardy *Hibiscus* were more freely branching and denser than plants of the cultivar Kopper King.
2. Plants of the new Hardy *Hibiscus* had smaller leaves than plants of the cultivar Kopper King.
3. Plants of the new Hardy *Hibiscus* flowered about seven to ten days earlier than plants of the cultivar Kopper King.
4. Plants of the new Hardy *Hibiscus* had smaller flowers than plants of the cultivar Kopper King.

5. Plants of the new Hardy *Hibiscus* and the cultivar Kopper King differed in flower color.

Plants of the new Hardy *Hibiscus* can be compared to plants of the *Hibiscus moscheutos* cultivar Morrison-Gilberg (VII), disclosed in U.S. Plant Pat. No. 14,313. In side-by-side comparisons conducted in Alva, Fla., plants of the new Hardy *Hibiscus* differed from plants of the cultivar Morrison-Gilberg (VII) in the following characteristics:

1. Plants of the new Hardy *Hibiscus* were shorter than plants of the cultivar Morrison-Gilberg (VII).
2. Plants of the new Hardy *Hibiscus* were more freely branching and denser than plants of the cultivar Morrison-Gilberg (VII).
3. Plants of the new Hardy *Hibiscus* and the cultivar Morrison-Gilberg (VII) differed in leaf color.

BRIEF DESCRIPTION OF THE PHOTOGRAPHS

The accompanying colored photographs illustrate the overall appearance of the new Hardy *Hibiscus,* showing the colors as true as it is reasonably possible to obtain in colored reproductions of this type. Colors in the photographs may differ slightly from the color values cited in the detailed botanical description which accurately describe the colors of the new Hardy *Hibiscus*.

The photograph at the bottom of the sheet comprises a side perspective view of a typical flowering plant of 'Brandy Punch' grown in a container.

The photograph at the top of the sheet comprises a close-up view of a typical flower of 'Brandy Punch'.

DETAILED BOTANICAL DESCRIPTION

The aforementioned photographs and following observations, measurements and values describe plants grown during the summer in Alva, Fla. in 1.5-gallon containers in a polypropylene-covered shadehouse and under conditions which closely approximate commercial Hardy *Hibiscus* production. During the production of the plants, day temperatures ranged from about 29° C. to about 35° C. and night temperatures ranged from about 21° C. to about 24° C. Plants were pinched one time and were about two months old when the photographs and the description were taken. In the description, color references are made to The Royal Horticultural Society Colour Chart, 1995 Edition, except where general terms of ordinary dictionary significance are used.

Botanical classification: *Hibiscus* hybrid cultivar Brandy Punch.

Parentage:

*Female, or seed, parent.*—*Hibiscus* hybrid cultivar Carafe Yogrenache, disclosed in U.S. Plant Pat. No. 17,571.

*Male or pollen parent.*—*Hibiscus* hybrid cultivar Kopper King, disclosed in U.S. Plant Pat. No. 10,793.

Propagation:

*Type.*—By vegetative terminal cuttings.

*Time to initiate roots, summer.*—About eight days at temperatures of 30° C.

*Time to initiate roots, winter.*—About ten days at temperatures of 21° C.

*Time to develop roots, summer.*—About 12 to 14 days at temperatures of 30° C.

*Time to develop roots, winter.*—About 18 to 21 days at temperatures of 21° C.

*Root description.*—Thick becoming fibrous and enlarged; white in color.

*Rooting habit.*—Freely branching.

Plant description:

*Plant form and growth habit.*—Upright and outwardly spreading plant habit. Vigorous growth habit.

*Branching habit.*—Freely branching, usually about four to five lateral branches develop after pinching.

*Plant height.*—About 33 cm.

*Plant diameter* (*area of spread*).—About 52 cm.

Lateral branch description:

*Length.*—About 29 cm.

*Diameter.*—About 1.2 cm.

*Internode length.*—About 2.5 cm.

*Strength.*—Strong.

*Texture.*—Smooth, glabrous.

*Color.*—146A tinted with 183A to 183B.

Foliage description:

*Arrangement.*—Alternate, single.

*Length.*—About 12.4 cm.

*Width.*—About 13 cm.

*Shape.*—Palmately lobed, mapleleaf-shaped.

*Apex.*—Acuminate; reflexing.

*Base.*—Cordate.

*Margin.*—Shallowly crenate.

*Texture, upper and lower surfaces.*—Smooth, glabrous.

*Venation pattern.*—Palmate.

*Color.*—Developing foliage, upper surface: 137A. Developing foliage, lower surface: 137C. Mature foliage, upper surface: 147A tinted with 183B; venation, 183A. Mature foliage, lower surface: 147B; venation, 147C.

*Petiole.*—Length: About 8.7 cm. Diameter: About 4 mm. Texture, upper and lower surfaces: Smooth, glabrous. Color, upper surface: 146A tinted with 183A to 183B. Color, lower surface: 146B.

Flower description:

*Flower arrangement.*—Flowers arranged singly originating from leaf axils. Lateral stems with typically one open flower and about six to seven flower buds. Flowers face mostly outwardly.

*Flower appearance.*—Large, rounded dark pink-colored flowers. Flowers last for about three days. Flowers persistent. Flowers not fragrant.

*Natural flowering season.*—Usually spring and summer or during periods of warm weather. Early flowering habit, plants begin flowering about nine weeks after pinching.

*Flower diameter.*—About 14 cm.

*Flower length* (*height*).—About 7 cm.

*Flower bud.*—Length: About 5.6 cm. Diameter: About 3.8 cm. Shape: Ovate. Color: Slightly more grey than 72D.

*Petals.*—Arrangement: Corolla consists of five petals that are fused at base; petals imbricate. Length: About 7.8 cm. Width: About 8.2 cm. Shape: Obovate to fan-shaped. Apex: Rounded. Base: Acute. Margin: Entire; slightly sinuate. Texture: Upper surface: Smooth, glabrous; slightly ridge. Lower surface: Smooth, glabrous; veins prominent. Color: When opening, upper surface: 71D. When opening, lower surface: More grey than 72D. Fully opened, upper surface: 74C; towards the base, 53A; venation, 71C. Fully opened, lower surface: 74D to slightly more grey than 74D; venation, 70D. With development, color becoming closer to 186C.

*Sepals.*—Appearance: Five sepals fused at the base into a star-shaped calyx. Length: About 3.1 cm. Width: About 2 cm. Shape: Elliptic to ovate. Apex: Acuminate. Margin: Entire. Texture, upper surface: Smooth, glabrous. Texture, lower surface: Smooth, glabrous; ridged veins. Color, upper surface: Close to 144B. Color, lower surface: Close to 144A.

*Bracts.*—Appearance: About ten to eleven fused at base. Length: About 2.5 cm. Width: About 2 mm. Shape: Lanceolate. Apex: Acute. Margin: Entire. Texture, upper and lower surfaces: Smooth, glabrous. Color, upper and lower surfaces: Close to 137A.

*Peduncles.*—Length: About 3.2 cm. Diameter: About 3.5 mm. Angle: About 45° from vertical. Strength: Strong. Texture: Smooth, glabrous. Color: 147A to 147B.

*Reproductive organs.*—Androecium: Stamen number: Numerous, about 90. Filament length: About 3.5 mm. Filament color: Close to 73C. Anther shape: Bi-lobed. Anther length: About 1.5 mm. Anther color: Close to 185A. Amount of pollen: Scarce. Pollen color: Close to 164C. Gynoecium: Pistil length: About 4.8 cm. Style length: About 4 cm. Style color: Towards the apex, close to 69B; mid-section and towards the base, close to 155D. Stigma appearance: Flat; five-lobed. Stigma color: 70C. Ovary color: Close to 145C.

*Seed/fruit.*—Seed and fruit production has not been observed.

Low temperature tolerance: Plants of the new Hardy *Hibiscus* have been observed be hardy to USDA Zone 5.

Pathogen/pest resistance: Plants of the new Hardy *Hibiscus* have not been observed to be resistant to pathogens and pests common to Hardy *Hibiscus*.

It is claimed:

1. A new and distinct *Hibiscus* plant named 'Brandy Punch' as illustrated and described.

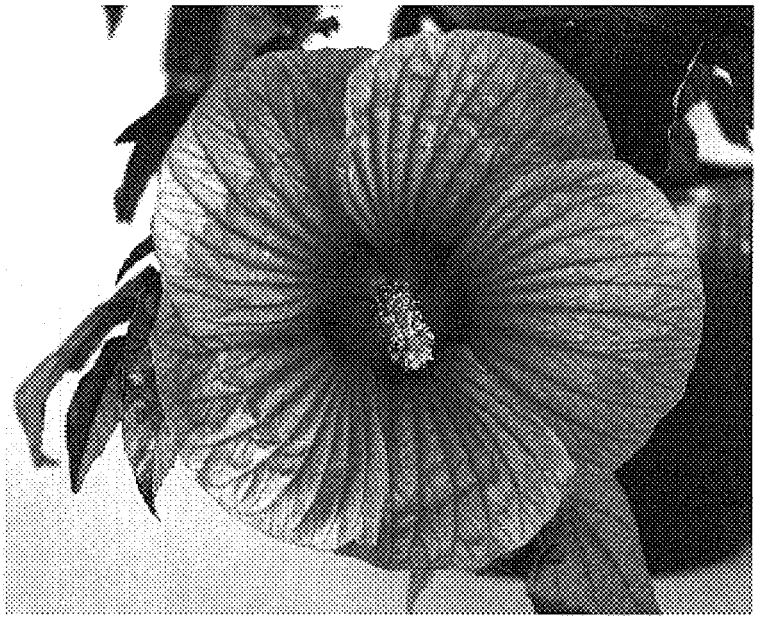
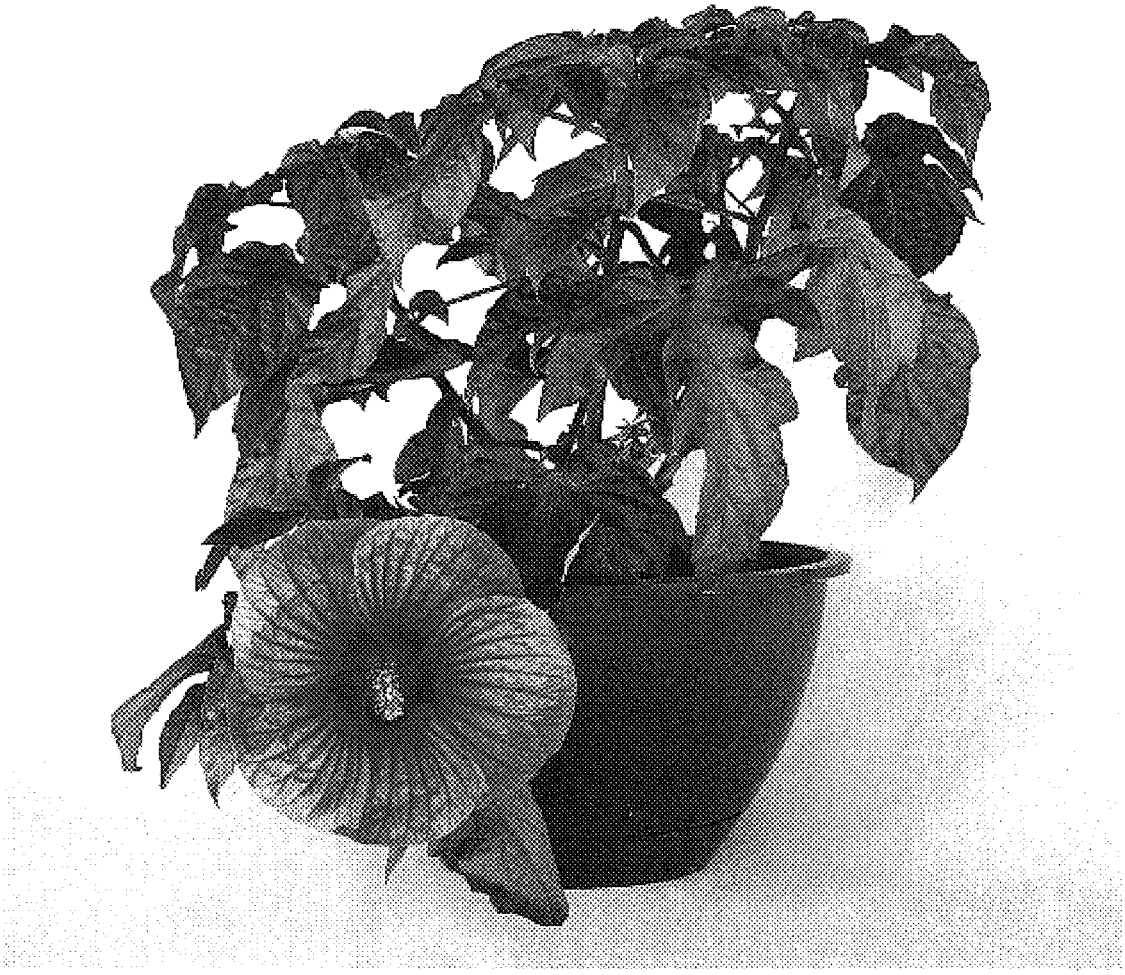

* * * * *